United States Patent

Simon

(12) United States Patent
(10) Patent No.: US 6,693,107 B1
(45) Date of Patent: Feb. 17, 2004

(54) PHARMACEUTICAL COMPOSITION USEFUL FOR THE TREATMENT OF TINNITUS AND HEARING LOSS

(76) Inventor: Shmuel Simon, Har Masada St. 47a, Ashdod (IL), 77711

(*) Notice: Subject to any disclaimer, the term of this patent is extended or adjusted under 35 U.S.C. 154(b) by 0 days.

(21) Appl. No.: 10/031,072

(22) PCT Filed: Jul. 9, 2000

(86) PCT No.: PCT/IL00/00405

§ 371 (c)(1), (2), (4) Date: Apr. 8, 2002

(87) PCT Pub. No.: WO01/05386

PCT Pub. Date: Jan. 25, 2001

(30) Foreign Application Priority Data

Jul. 15, 1999 (IL) .................................................. 130968

(51) Int. Cl.$^7$ ..................... A61K 31/52; A61K 31/505
(52) U.S. Cl. ..................... 514/266; 514/258; 514/262
(58) Field of Search .................. 514/258, 262, 514/266

(56) References Cited

FOREIGN PATENT DOCUMENTS

| EP | 0 063 381 A | 10/1982 |
| EP | 0 463 756 A | 1/1992 |
| WO | 94 28902 A | 12/1994 |
| WO | 99 02161 A | 1/1999 |
| WO | 99 21558 A | 5/1999 |

*Primary Examiner*—Zohreh Fay
(74) *Attorney, Agent, or Firm*—Lowe Hauptman Gilman & Berner LLP

(57) ABSTRACT

The present invention relates to the use of the compounds of formula (II) or any pharmaceutically acceptable salt thereof, in the preparation of pharmaceutical composition useful for decreasing or eliminating tinnitus and for decreasing hearing loss, wherein $R^1$, $R^2$, $R^3$ and $R^4$ are independently selected from the group of H, methyl, ethyl, propyl or isopropyl.

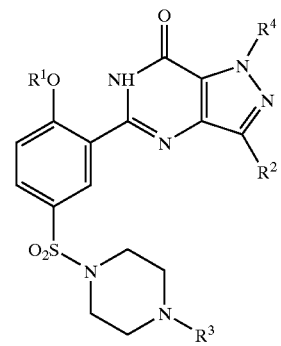

(II)

16 Claims, No Drawings

PHARMACEUTICAL COMPOSITION USEFUL FOR THE TREATMENT OF TINNITUS AND HEARING LOSS

FIELD OF THE INVENTION

The present invention relates to a pharmaceutical composition useful for the treatment of tinnitus and hearing loss. More specifically the present invention relates to pharmaceutical composition for use in the treatment of tinnitus and hearing loss irrespective of their etiology, containing as an active ingredient sildenafil and related compounds.

BACKGROUND OF THE INVENTION

The condition known as tinnitus refers to the subjective perception of sound when actually no objective sound exists and is often described as ringing in the ears. It is a symptom that may be associated with numerous pathological conditions arising from different mechanisms. However, in most cases, the etiology of tinnitus is unknown. It is usually associated with an ear disorder and often accompanied by hearing loss. The sound of tinnitus may have different characteristics and is invariably disturbing to the patient. Tinnitus is a prevalent symptom in the adult population, probably affecting more than 10% of adults. Unfortunately, despite the many attempts described in the professional literature to manage tinnitus, none is really effective in eliminating this disturbing symptom. Some methods, psychological, prosthetic and pharmaceutical, provide only limited relief. Sildenafil citrate (I), 1-[[3-(6,7-dihydro-1-methyl-7-oxo-3-propyl-1H-pyrazolo [4,3-d]pyrimidin-5-yl)-4-ethoxyphenyl]sulfonyl]4-methylpiperazine citrate, known by the commercial name Viagra, is prescribed for the treatment of erectile dysfinction.

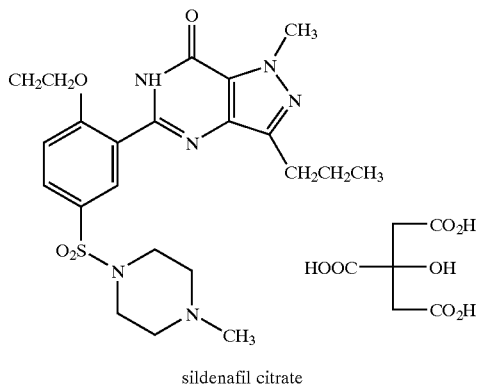

sildenafil citrate

The mechanism of sildenafil action is believed to be through inhibition of the enzyme phosphodiesterase type 5. The latter normally degrades the second messenger cyclic guanosine monophosphate (cGMP), which is produced, among others, in the normal penile tissue during the erectile response. Sildenafil thus increases the concentrations of cGMP and prolongs its effective life span in the tissue and by doing so, augments the physiological response during erection. Phosphodiesterase type 5 is also found in other tissues and its inhibition can therefore be expected to enhance the physiological or pathophysiological response of such tissues.

Surprisingly it was found in the present invention that sildenafil is effective in reducing tinnitus in patients suffering from tinnitus and ameliorating hearing loss.

It is the object of the present invention to provide a pharmaceutical composition useful for decreasing or even eliminating tinnitus and for ameliorating hearing loss.

SUMMARY OF THE INVENTION

The present invention relates to the use of sildenafil and related compounds of the formula II

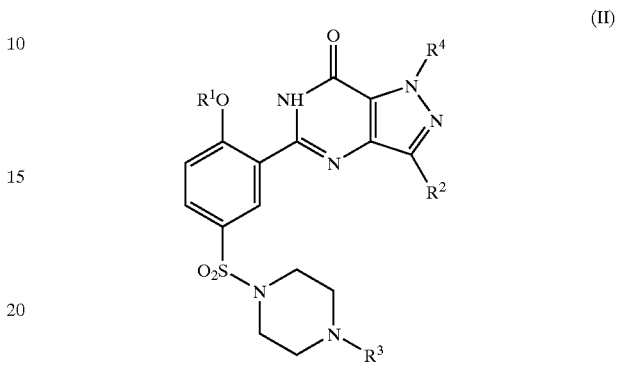

or any pharmaceutically acceptable salt thereof, in the preparation of pharmaceutical composition useful for decreasing or eliminating tinnitus and for decreasing hearing loss, wherein R1, R2, R3 and R4 are independently selected from the group of H, methyl, ethyl, propyl or isopropyl.

In a preferred embodiment the pharmaceutically acceptable salt is selected from the group consisting of citrate, oxalate, acetate, maleate, malonate, fumarate, succinate, tosylate, mesylate, hydrochloride, hydrobromide, sulfate, phosphate, methanesulfonate, toluenesulfonate or mixtures thereof.

In a preferred embodiment of the present invention R1is ethyl, R2 is propyl and R3 and R4 are independently selected from H or methyl or are both methyl groups. In another preferred embodiment the compound is sildenafil citrate (I).

The pharmaceutical compositions prepared according to the present invention contain a compound of formula I or II as an active ingredient in an effective amount and any pharmaceutically acceptable carrier or diluent, for decreasing or eliminating of tinnitus and for decreasing hearing loss. The present invention further includes a method for treating tinnitus and hearing loss in patients who are in need of such a treatment by administrating to said patients the pharmaceutical composition of the present invention as frequently as needed preferably in the range of 2–200 mg and more preferably in the range of 10 to 50 mg daily to weekly.

The pharmaceutical composition of the present invention can be prepared for oral administration in the form of a tablet, a capsule, a troche, a pill, a lozenge, a cachet, a powder, granules, a syrup, a solution, an emulsion or suspension or for parenteral administration in the form of a solution wherein the carrier is a liquid and the composition is a solution or suspension, or for rectal administration in the form of suppository, or for topical administration in the form of solution, cream, ointment, lotion, patch and the like. Most preferably the pharmaceutical composition of the present invention is administered orally.

The solid oral compositions of the present invention can be prepared by conventional methods known in the art. The active ingredient can be mixed with any conventional pharmaceutically acceptable filler (carrier) such as lactose, sucrose, mannitol, cellulose or mixtures thereof. Additional pharmaceutical excipients can be added. Preferably the pharmaceutical excipients are selected from the group consisting of binders, disintegrants, lubricants or mixtures thereof. Preferably the binder is acacia, alginic acid, sodium alginate, gelatin, polyvinylpyrollidone, cellulose derivatives, or mixtures thereof. The disintegrant is preferably starch, starch derivative, alginic acid, sodium alginate, or mixtures thereof. The lubricant is preferably magnesium stearate or stearic acid. The tablet or pill may be further coated by sugar coating, enteric coating or film coating using conventional methods known in the art.

The liquid preparations of the present invention are preferably aqueous solutions such as syrups or elixirs, aqueous or oily suspensions, or emulsions. The liquid preparations may be prepared using any pharmaceutically acceptable vehicle. The liquid preparations may contain conventional additives such as flavoring agents, coloring agents, preservatives, antioxidants or edible oils. For suspensions preparation, suitable suspending agents such as acacia, methylcellulose, sodium carboxymethylcellulose, sorbitol, gelatin, tragacanth, aluminum stearate, sodium alginate, or mixtures thereof are used. Additional excipients such as wetting agents or flocculating agents may be added. Non-aqueous suspension formulations are prepared using oily vehicles such as coconut oil or any other pharmaceutically acceptable edible oil.

The emulsion preparations are formulated using emulsifying agents. Preferably at least one emulsifying agent is used. The emulsifying agents are preferably polyoxyethylene sorbitan monolaurate (Tween 20), polyoxyethylene sorbitan monopalmitate (Tween 40), polyoxyethylene sorbitan monostearate (Tween 60), polyoxyelthylene sorbitan monooleate. (Tween 80), polyoxyethelene lauryl ether (Brij 35), sodium lauryl sulfate, sorbitan trioleate (Span 85, Aracel 85), sorbitan tristearate (Span 65), sorbitan monooleate (Span 80), propylene glycol monostearate, sorbitan sequioleate (Aracel C), sorbitan monostearate (Span 60, Aracel 60), sorbitan monopalmitate (Span 40, Aracel 40), lecitin or mixtures thereof. Any other pharmaceutically acceptable emulsifying agent known in the art may be used. Orally administered liquid compositions may also be prepared as dry products for reconstitution before use.

The injectable preparations of the present invention may be administered by intravenous, intramuscular, subcutaneous or other route. The injectable preparations may be prepared with aqueous or non-aqueous vehicles. Salts or buffering agents suitable for parenteral use may be added. The injectable preparations may additionally contain water miscible solvents such as ethanol, propylene glycol, polyethylene glycol or mixtures thereof. Various oils suitable for parenteral administration may be used.

Suppositories for rectal administration may contain carriers and other additives such as cacao butter, witepsol, polyethylene glycol, gelatin, glycerin; alcohols and esters.

EXAMPLES

Example 1

A 56 year old man suffering for several years from severe tinnitus and hearing loss in his right ear had repeatedly sought medical advice and tried many alleged therapies for his tinnitus, none of which was effective. His past medical history reveals thyroid carcinoma, 2 years ago, for which he was successfully operated. Other than that he is in good health and receives no medications. Recently he was prescribed sildenafil citrate for improving his sexual performance. Unexpectedly, he noticed amelioration of the tinnitus, which eventually nearly disappeared. An intentional test was made to stop the medication, which resulted in return of the tinnitus within a period of 2–3 weeks from cessation of the sildenafil citrate. A rechallenge with sildenafil citrate, 25 mg twice weekly, again reduced the severity of tinnitus within a week and proceeded to almost complete disappearance of the symptom. He continues on sildenafil citrate and is now practically tinnitus-free. He also reports significant improvement in his hearing.

An audiogram performed after several months treatment with sildenafil citrate showed marked improvement. For instance, at frequencies of 500–1000 Hz, hearing in his right ear improved from 50–55 dB to 30 dB.

Example 2

A 57 year old woman known to have bilateral tinnitus and hearing loss for more than 20 years. Other than hypertension, for which she is treated, she is in good health. She was prescribed sildenafil citrate, 25 mg daily, for the tinnitus. Starting after the 5th daily dose she reported marked reduction in her tinnitus, which persisted for as long as she took the drug.

What is claimed is:

1. A method for treating tinnitus or hearing loss or both in a patient in need thereof, which comprises administering to said patient an effective amount of a compound of formula (II):

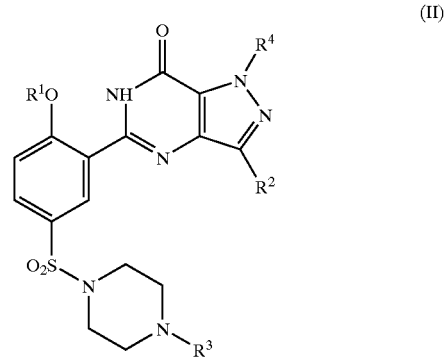

or a pharmaceutically acceptable salt thereof, wherein $R^1$, $R^2$, $R^3$ and $R^4$ are independently selected from the group consisting of hydrogen, methyl, ethyl, propyl and isopropyl.

2. The method of claim 1, wherein the pharmaceutically acceptable salt is selected from the group consisting of citrate, oxalate, acetate, maleate, malonate, fumarate, succinate, tosylate, mesylate, hydrochloride, hydrobromide, sulfate, phosphate, methanesulfonate, toluenesulfonate and mixtures thereof.

3. The method of claim 1, where in $R^1$ is ethyl, $R^2$ propyl, and $R^3$ and $R^4$ are independently selected from the group consisting of hydrogen and methyl.

4. The method of claim 1, wherein $R^1$ is ethyl, $R^2$ is propyl, and $R^3$ and $R^4$ are each methyl.

5. The method of claim 1, wherein the compound of the formula (II) is sildenafil citrate.

6. The method of claim 1, wherein the effective amount of the compound of the formula (II) is in the range of 2 to 200 mg.

7. The method of claim 1, wherein the compound of the formula (II) is administered as a pharmaceutical composition comprising one or more compounds of the formula (II) and a pharmaceutically acceptable carrier.

8. The method of claim 1, wherein the compound of the formula (II) is administered orally in a form selected from the group consisting of a tablet, capsule, troche, pill, lozenge, cachet, power, granules, syrup, solution, emulsion and suspension.

9. The method of claim 1, wherein the compound of the formula (II) is administered parenterally in the form of solution or suspension.

10. The method of claim 1, wherein the compound of the formula (II) is administered rectally in the form of a suppository.

11. The method of claim 1, wherein the compound of the formula (II) is administered topically in a form selected from the group consisting of a solution, cream, ointment, lotion and patch.

12. The method of claim 6, wherein said effective amount of the formula (II) is in a range of 2 to 200 mg administered daily to weekly.

13. The method of claim 12, wherein said effective amount is the range of from 10 to 50 mg administered daily to weekly.

14. The method of claim 1, which is for treating tinnitus.

15. The method of claim 1, which is for treating hearing loss.

16. The method of claim 1, which is for treating both tinnitus and hearing loss.

* * * * *